(12) United States Patent
Poulose

(10) Patent No.: US 12,349,862 B2
(45) Date of Patent: Jul. 8, 2025

(54) DEVICE FOR IMPROVING ERGONOMICS OF AN ENDOSCOPIC CONTROL HANDLE

(71) Applicant: Ohio State Innovation Foundation, Columbus, OH (US)

(72) Inventor: Benjamin K. Poulose, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 681 days.

(21) Appl. No.: 17/597,783

(22) PCT Filed: Jan. 24, 2022

(86) PCT No.: PCT/US2022/070298
§ 371 (c)(1),
(2) Date: Jan. 24, 2022

(87) PCT Pub. No.: WO2022/170297
PCT Pub. Date: Aug. 11, 2022

(65) Prior Publication Data
US 2023/0309790 A1    Oct. 5, 2023

Related U.S. Application Data

(60) Provisional application No. 63/220,070, filed on Jul. 9, 2021, provisional application No. 63/144,494, filed on Feb. 2, 2021.

(51) Int. Cl.
*A61B 1/00* (2006.01)
*A61B 1/005* (2006.01)

(52) U.S. Cl.
CPC ........ *A61B 1/00042* (2022.02); *A61B 1/0014* (2013.01); *A61B 1/0052* (2013.01)

(58) Field of Classification Search
CPC .. A61B 1/00042; A61B 1/0014; A61B 1/0052
See application file for complete search history.

(56) References Cited

U.S. PATENT DOCUMENTS 8,092,373 B1 *  1/2012  Papouras ........... A61B 1/00105
                                                            600/102
8,100,825 B2 *  1/2012  Moriyama ........... A61B 1/0052
                                                            600/149

(Continued)

FOREIGN PATENT DOCUMENTS

EP    2316328         5/2012
EP    1518492 B1      5/2017

OTHER PUBLICATIONS

Australian Intellectual Property Office. Examination Report No. 1. Issued in AU Application No. 2022217272 on May 7, 2024. 5 pages.

(Continued)

*Primary Examiner* — Anh Tuan T Nguyen
*Assistant Examiner* — Shankar Raj Ghimire
(74) *Attorney, Agent, or Firm* — Meunier Carlin & Curfman LLC

(57) ABSTRACT

An endoscope has a control handle having angulation knobs, wherein the angulation knobs are oversized permitting the user to access the oversize angulation knobs without stressing the thumb. A control handle attachment secures to the control handle and urges the hand into a neutral anatomic position.

9 Claims, 12 Drawing Sheets

(56) References Cited

U.S. PATENT DOCUMENTS

| | | | | |
|---|---|---|---|---|
| 2003/0187328 | A1* | 10/2003 | Seki | A61B 1/0052 600/146 |
| 2006/0069311 | A1 | 3/2006 | Sullivan et al. | |
| 2006/0258908 | A1* | 11/2006 | Stefanchik | A61B 1/018 600/121 |
| 2010/0280309 | A1* | 11/2010 | von Pechmann | A61B 17/42 600/37 |
| 2011/0065989 | A1* | 3/2011 | Sarvazyan | A61B 1/31 600/117 |
| 2013/0036528 | A1* | 2/2013 | Wilson | A41D 19/0034 2/160 |
| 2014/0275784 | A1* | 9/2014 | Joyce | A61M 16/0493 600/114 |
| 2017/0209024 | A1* | 7/2017 | Weitzner | A61B 1/0661 |
| 2017/0215696 | A1* | 8/2017 | Harrah | A61B 18/24 |
| 2018/0042603 | A1* | 2/2018 | Mitelberg | A61B 1/00101 |
| 2018/0284468 | A1* | 10/2018 | Parker | G02B 30/37 |
| 2020/0323418 | A1* | 10/2020 | Narayana | A61B 1/00066 |
| 2022/0160213 | A1* | 5/2022 | Uspenski | A61B 1/00087 |
| 2022/0167881 | A1* | 6/2022 | Adamson | A61B 1/046 |
| 2023/0309790 | A1* | 10/2023 | Poulose | A61B 1/0014 600/146 |

OTHER PUBLICATIONS

International Search Report and Written Opinion issued for Application No. PCT/US2022/070298, dated Jul. 1, 2022.

Gastrointestinal Endoscopic Devices Market Analysis, Size, Trends | Global |2019-2025 | MedSuite. iData Research https://idataresearch.com/product/gastrointestinal-endoscopic-devices-market/.

Berguer, R. & Hreljac, A. The relationship between hand size and difficulty using surgical instruments: a survey of 726 laparoscopic surgeons. Surg. Endosc. 18, 508-512 (2004).

Ratuapli, S. et al. Kinematic analysis of wrist motion during simulated colonoscopy in first-year gastroenterology fellows. Endosc. Int. Open 03, E621-E626 (2015).

Siau, K. & Anderson, J. T. Ergonomics in endoscopy: Should the endoscopist be considered and trained like an athlete? Endosc. Int. Open 07, E813-E815 (2019).

Austin, K. et al. Musculoskeletal Injuries Are Commonly Reported Among Gastroenterology Trainees: Results of a National Survey. Dig. Dis. Sci. 64, 1439-1447 (2019).

Shergill, A. K., McQuaid, K. R. & Rempel, D. Ergonomics and GI endoscopy. Gastrointest, Endosc. 70, 145-153 (2009).

Cappell, M. S. & Co, M. Endoscopes for endoscopists with small hands: a call to meet an unmet demand. Gastrointest. Endosc. 78, 670-672 (2013).

Shergill, A. K. & McQuaid, K. R. Ergonomic endoscopy: An oxymoron or realistic goal? Gastrointest. Endosc. 90, 966-970 (2019).

Communication pursuant to Rule 164(1) EPC for EP Application No. 22750605.2 dated Feb. 18, 2025, 18 pages.

* cited by examiner

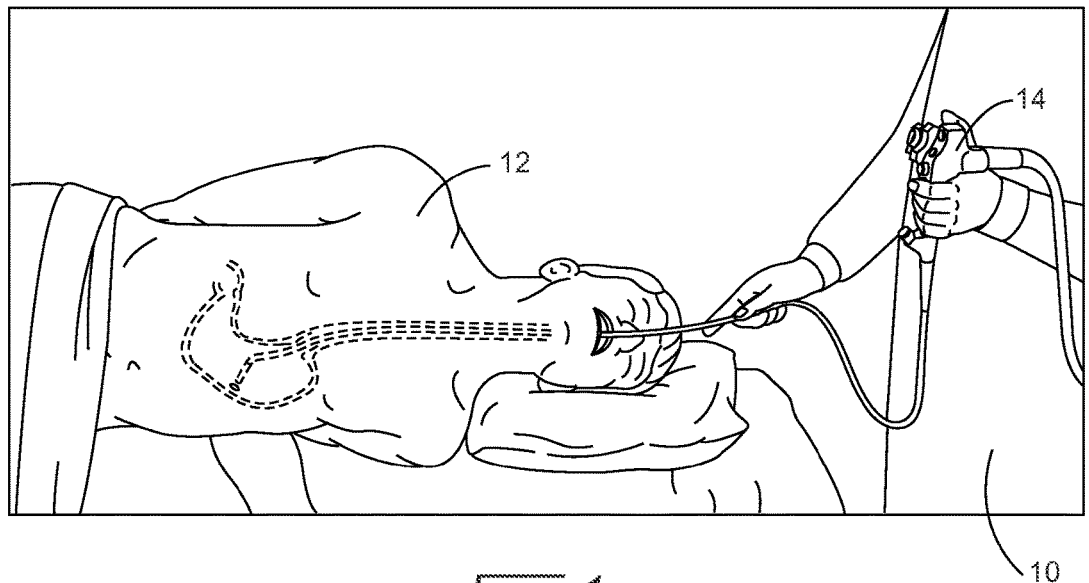
FIG. 1
PRIOR ART
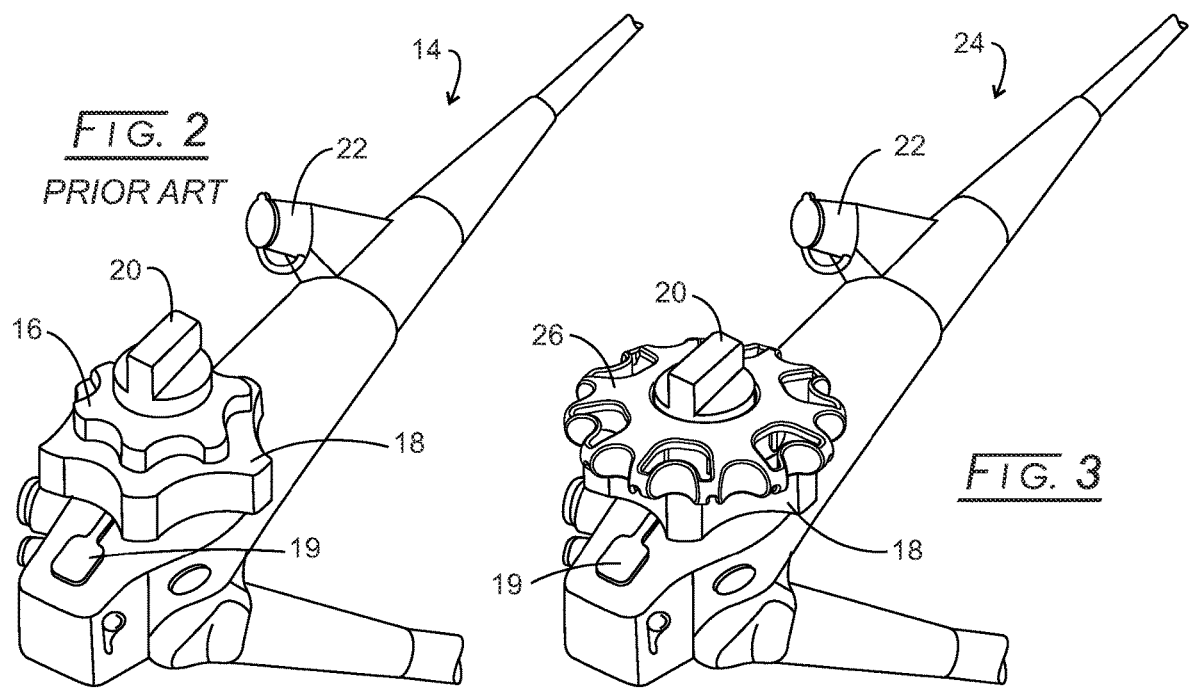
FIG. 2
PRIOR ART
FIG. 3

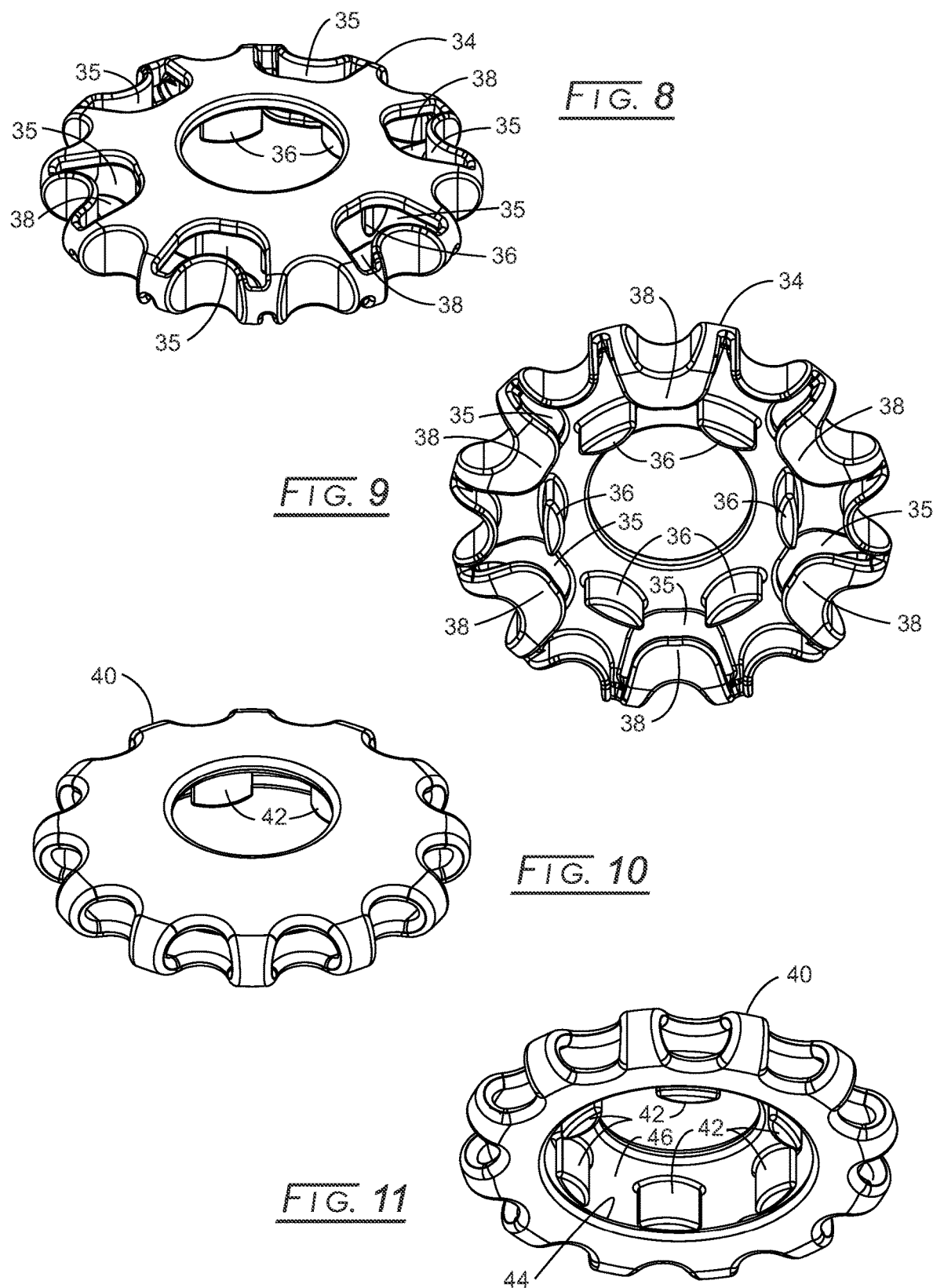

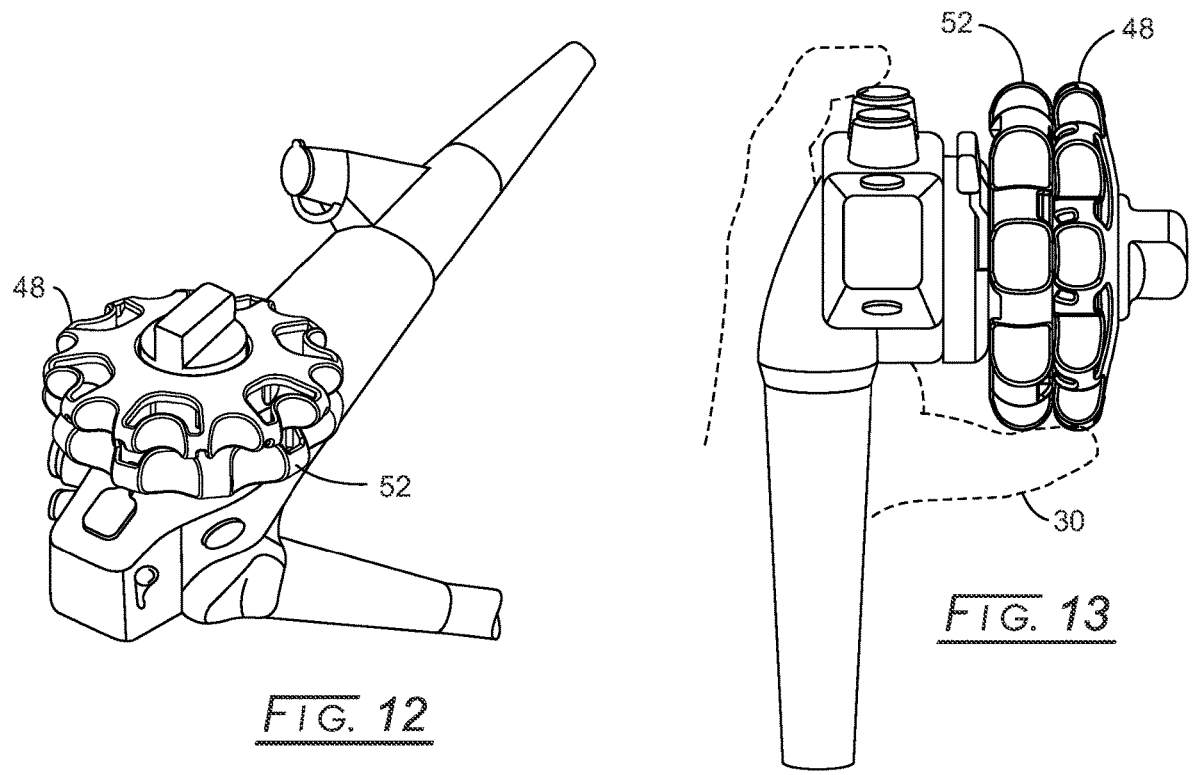
FIG. 12
FIG. 13
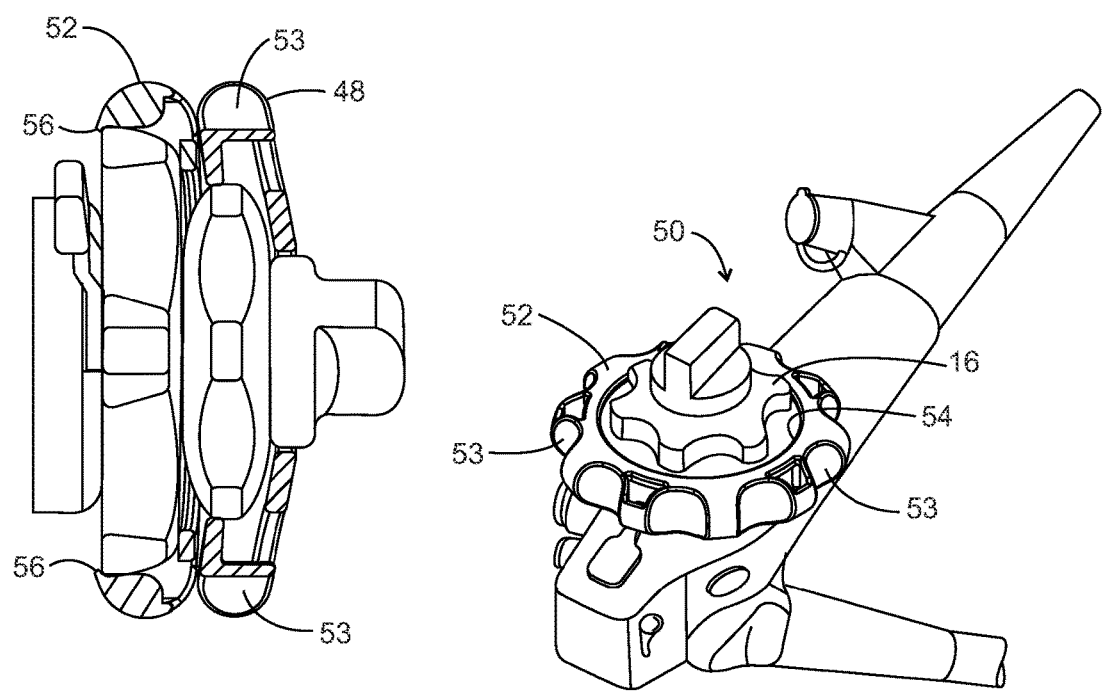
FIG. 14
FIG. 15

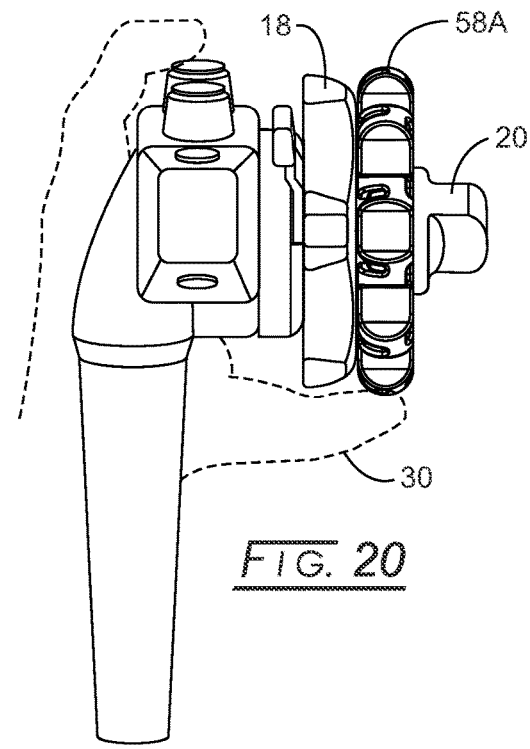
FIG. 20
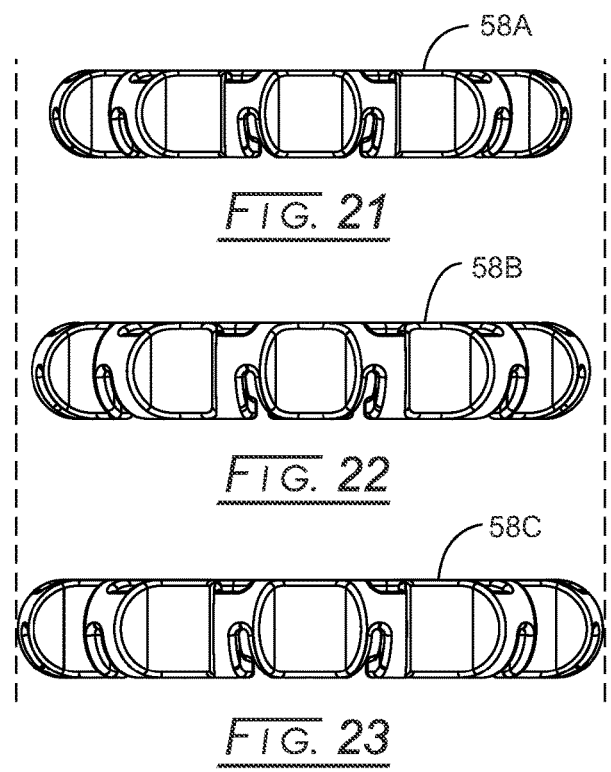
FIG. 21
FIG. 22
FIG. 23
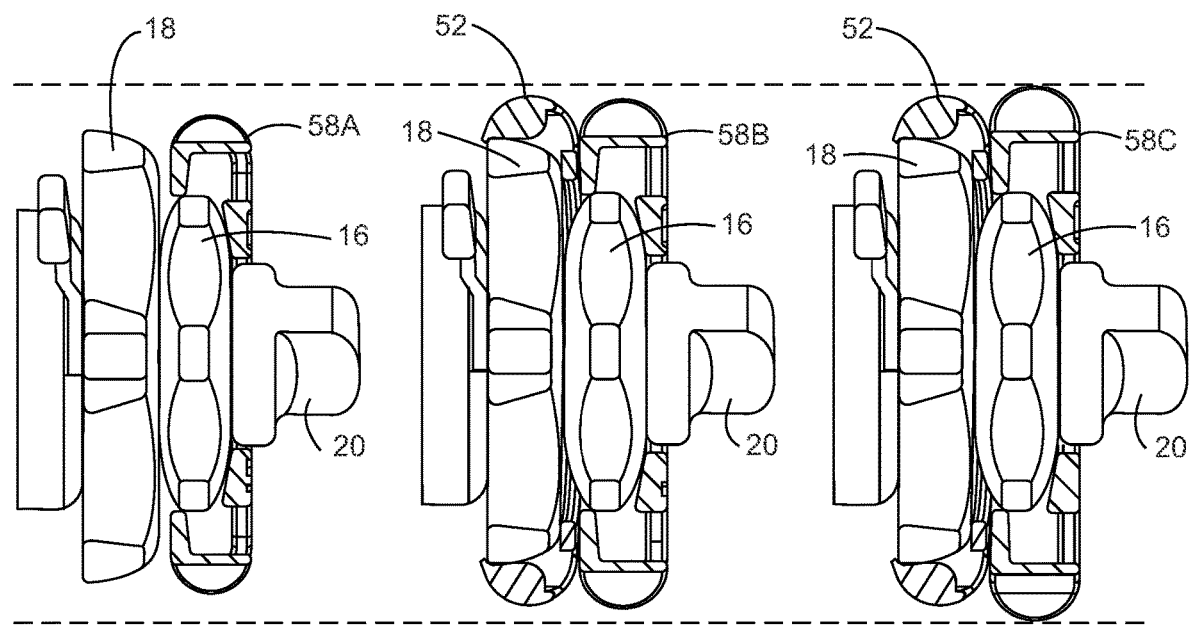
FIG. 24    FIG. 25    FIG. 26

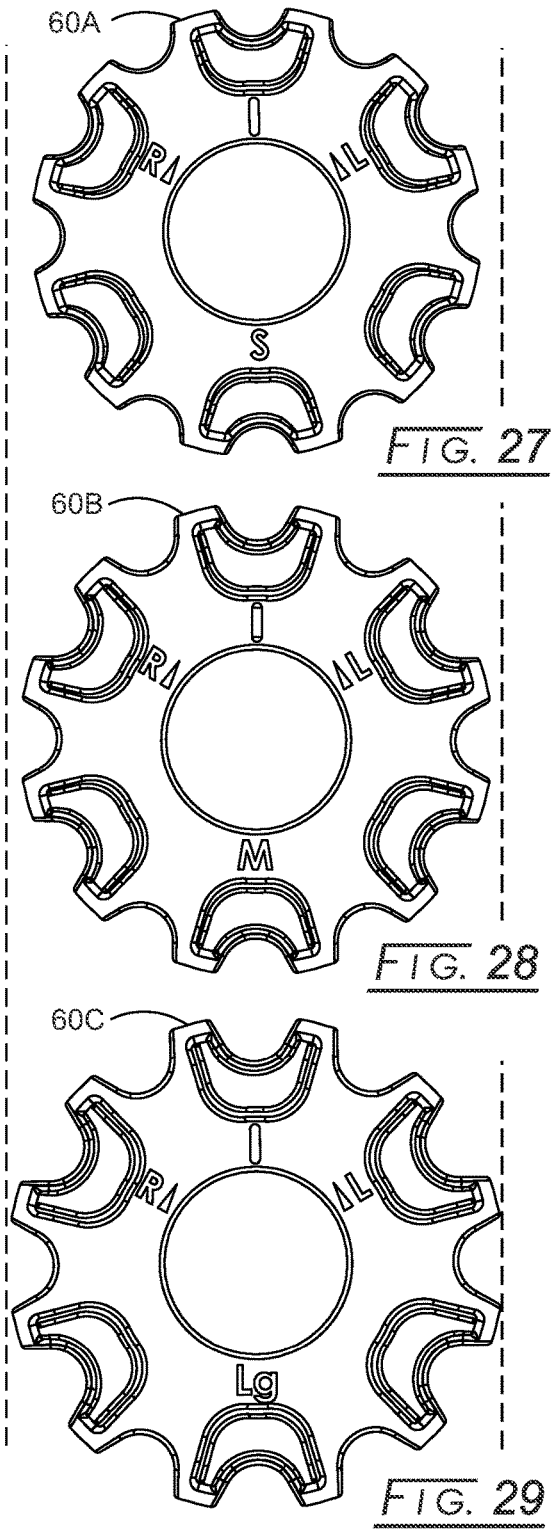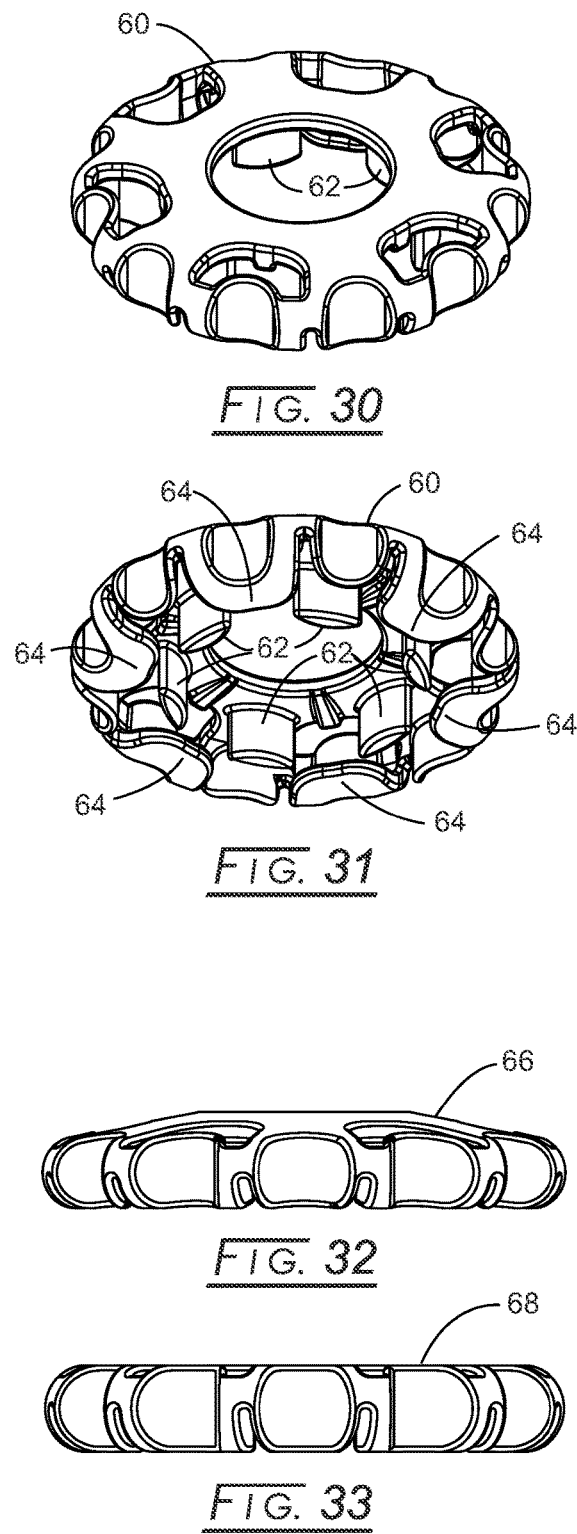

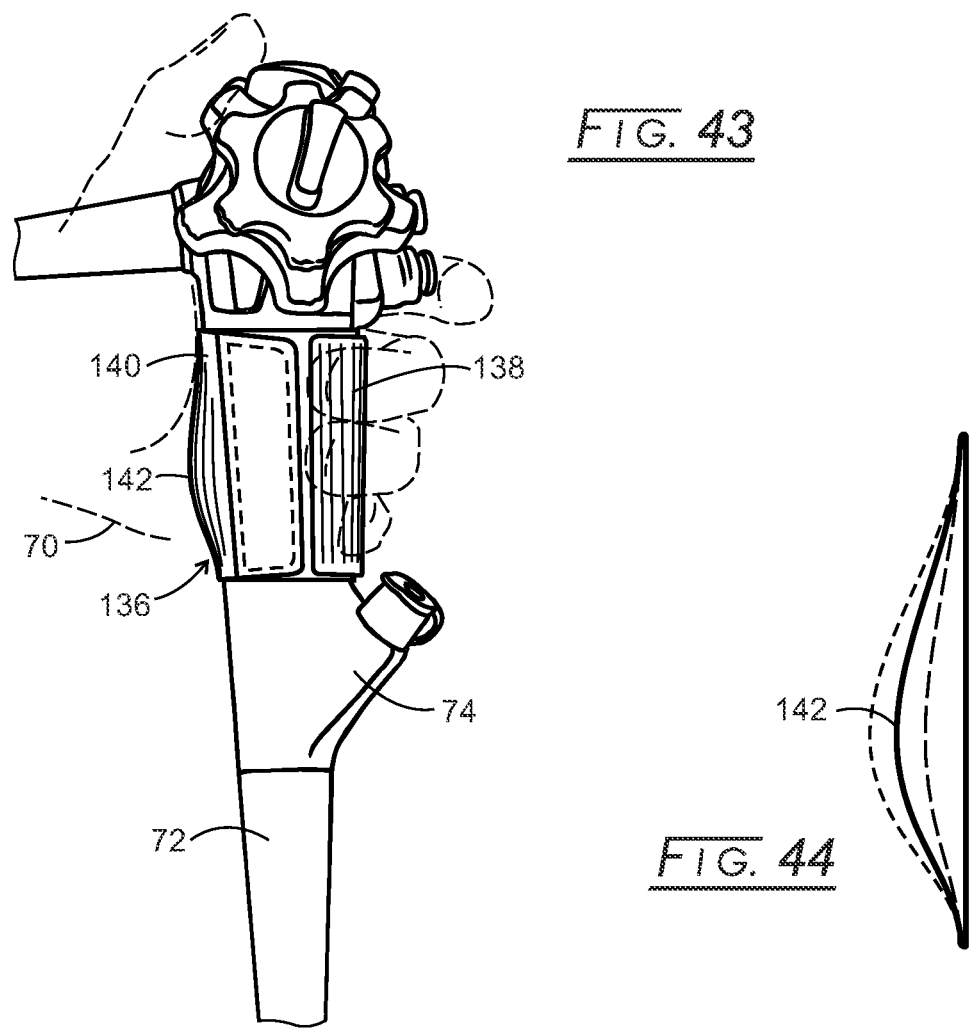
FIG. 43
FIG. 44
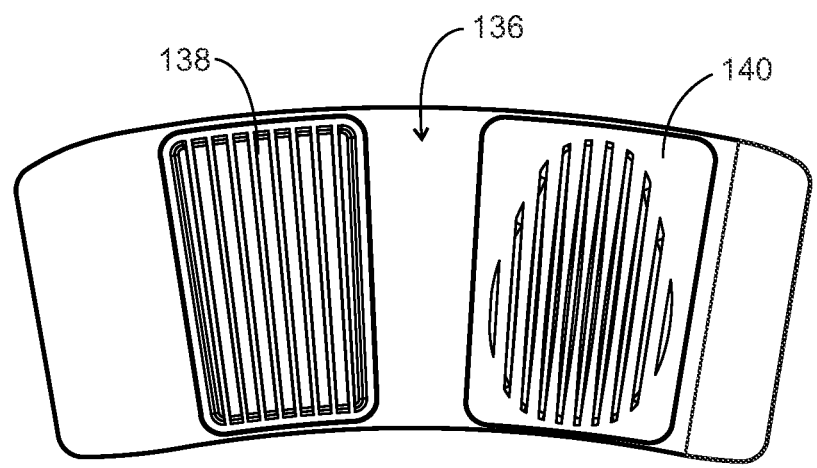
FIG. 45

DEVICE FOR IMPROVING ERGONOMICS OF AN ENDOSCOPIC CONTROL HANDLE

CROSS-REFERENCE TO RELATED APPLICATIONS

This application claims benefit of provisional application Ser. No. 63/144,494 filed on Feb. 2, 2021, and 63/220,070 filed on Jul. 9, 2021. The disclosures of these provisional applications are express incorporated herein by reference.

STATEMENT REGARDING FEDERALLY SPONSORED RESEARCH AND DEVELOPMENT

Not applicable.

THE NAMES OF THE PARTIES TO A JOINT RESEARCH AGREEMENT

Not applicable.

REFERENCE TO A "SEQUENCE LISTING," A TABLE, OR A COMPUTER PROGRAM

Not applicable.

STATEMENT REGARDING PRIOR DISCLOSURES BY THE INVENTOR OR A JOINT INVENTOR

Not applicable.

BACKGROUND OF THE INVENTION

Current State:

Flexible endoscopy is one of the most common procedures performed in medicine today. Applications include diagnostic and therapeutic maneuvers for gastrointestinal, pulmonary, and urologic diseases. For gastrointestinal diseases, over 32 million endoscopic procedures are performed on a yearly basis in the United States alone, making it one of the most common medical procedures.[1] Successful, safe, and efficient performance of these procedures requires the appropriate training, experience, and manual dexterity similar to any technically based field. Individual endoscopists may perform tens of thousands of endoscopic procedures over their careers to diagnose and treat a variety of diseases. Current flexible endoscope equipment comes in a single size, assuming a 'one size fits all' paradigm.

The standard technique for gastrointestinal flexible endoscopy requires the endoscopist's right hand to manipulate the insertion tube while the left hand manipulates the control handle, actuator buttons, and two control wheels (FIG. 1). These control wheels govern a critical function—directional control—of the flexible endoscope (FIG. 2). A larger 'up-down' control wheel manipulates the endoscope tip along one axis and a smaller 'left-right' control wheel manipulates the endoscope tip along another axis perpendicular to that controlled by the larger up-down control wheel. Twisting and angling the control handle also allows endoscope manipulation to help with procedural efficiency. Most flexible endoscopes, especially those used in gastrointestinal endoscopy, utilize this two-control wheel paradigm for directional control with simultaneous control handle manipulation, placing significant strain and burden on the endoscopist's left hand. Furthermore, the design for the control handle and control wheels are standardized ('one size fits all') for a given manufacturer across different flexible endoscope platforms intended for different uses. This standardization allows for ease and reproducibility in manufacturing and familiarity to the endoscopist.

A single device is available on the market (U.S. Pat. No. 8,100,825) to assist with ergonomics in gastrointestinal endoscopy. This device consists of a single small wheel attachment. Two patents exist in terms of control handle augmentation. U.S. Pat. No. 8,092,373 consists of a rigid and modular piece that snaps into place onto the endoscope control handle. U.S. Publication US 2020/0323418 also consists of a rigid piece that snaps into place onto the endoscope control handle to improve ergonomics.

Shortfalls of Current State:

Potential Endoscopist Injuries—The lack of an array of native flexible endoscope control component sizes, combined with flexible endoscopy being a highly repetitive procedural field, can lead to musculoskeletal injury over time.[4] In a survey of over 1500 trainees in gastroenterology, 20% reported having musculoskeletal injuries.[5] Female gender was the sole factor associated with a higher rate of injury. In addition, gastroenterologists, who perform the majority of gastrointestinal flexible endoscopy, are at risk of 'overuse injuries' including carpal tunnel syndrome, DeQuervain's tenosynovitis, and lateral epicondylitis.[6] These studies highlight the problem faced by endoscopists, which places women at a particular disadvantage compared to men with the use of flexible endoscopes due to generally smaller hand sizes. These problems have reached significant levels, even prompting practicing endoscopists to demand changes in the design of current endoscopes.[7]

Ergonomic Inefficiencies—Flexible endoscopy standard technique involves the endoscopist's right hand to manipulate the insertion tube while the left hand manipulates the control handle, actuator buttons, and two control wheels (FIG. 1). This configuration allows for the most efficient endoscopic control as each hand can remain in place on one component of the endoscope (i.e., right hand on the insertion tube and left hand on the control handle). In this configuration, the left-hand thumb is expected to manipulate both the up-down and left-right endoscopic control wheels (FIG. 4) while simultaneously angling and moving the control handle. However, if the endoscopist's left hand and/or finger sizes are not large enough to manipulate both endoscopic control wheels using the left hand alone, the right hand is then required to be removed from the insertion tube to briefly manipulate the smaller left-right control wheel. Twenty-three percent of gastroenterologists experience some difficulty in reaching the two control wheels with a single hand during colonoscopy, with women facing a significant disadvantage compared to men.[7] In addition, significant fatigue and strain can be experienced with the current paradigm in endoscopic control handle design with the left hand forced to operate in an unnatural position. The entire weight of the control handle is placed on the left hand without support to offset or redistribute this weight during the performance of an endoscopic procedure. Specific steps have been outlined to create more ergonomically efficient gastrointestinal flexible endoscopy including modifications to endoscopic control wheels and better control handle designs.[8]

Lack of Comprehensive Ergonomic Solution—Although the proposed solutions do begin to address ergonomics in endoscopy, none of these solutions provide a comprehensive ergonomic system that works in a concerted fashion to reduce hand/finger strain and fatigue. A comprehensive ergonomic solution would encompass customizable components for both control wheel assists and control handle accessories that work together to improve ergonomics for each endoscopist and their unique hand anatomy.

No Soft Control Handle Assist Device—None of these proposed solutions provides a completely soft control handle augmentation device or soft hand strap as part of a comprehensive ergonomic system. A soft goods solution provides the most conformable device that allows maximal adaptability for the endoscopists hand while minimize damage to the endoscope itself.

Despite an ever-growing body of scientific literature highlighting the health threat to flexible endoscopists and ergonomic inefficiencies caused by the lack of varying sizes of endoscopic control mechanisms, nothing has effectively been done to change the current state. This continues to place female endoscopists at a particular disadvantage compared to their male counterparts, given the generally smaller hand and/or finger sizes of women.

BRIEF SUMMARY OF THE INVENTION

Endoscopes have a control handle having a top angulation knob and a lower larger angulation knob wherein one of the angulation knobs controls up and down movement of the endoscope insertion tube and the other angulation knob controls the left and right movement of the insertion tube. One aspect disclosed herein includes a top angulation knob cover fitting over and moving the smaller top angulation knob, the top angulation knob cover being at least as large in diameter as the lower angulation knob. A further improvement includes a lower angulation knob cover fitting over the lower angulation know and moving the lower angulation knob. Thus, either angulation knob or both knobs can have a knob cover fitting thereover.

The angulation knob covers make the effective size of the angulation knob over which they fit larger so that a user can access the "oversize" angulation knobs without excessively bending or stretching the thumb of the user.

Also disclosed are endoscope control handle attachments secured to the control handle, urging the hand into a neutral anatomic position. In particular a control handle assembly has a top angulation knob and a lower angulation knob wherein one of the angulation knobs controls up and down movement of the endoscope insertion tube and the other angulation knob controls the left and right movement of the insertion tube, wherein the attachment is an elastic member, which advantageously is an elastomeric member. The elastic member may be a foamed elastic member. One configuration of the elastic member is such that it wraps around the control handle, which then is grasped by the left hand. Another configuration of the elastic member is a strap that connects the top of the endoscope control handle to the base of the biopsy channel. In such a configuration, the left hand of the endoscope is allowed to fit between the elastic member and the control handle, redistributing the weight of the control handle in an ergonomically advantageous manner across the left hand. The angulation know covers fit thereover and can be used in combination the elastic member(s). The components are intentionally designed to work separately or in conjunction with each other to maximize ergonomic advantage.

BRIEF DESCRIPTION OF THE SEVERAL VIEWS OF THE DRAWINGS

For a fuller understanding of the nature and advantages of the present method and process, reference should be had to the following detailed description taken in connection with the accompanying drawings, in which:

FIG. 1 is an isometric view of a patient in repose on their side having an endoscopic procedure with access via the oral cavity;

FIG. 2 is an isometric view of a current commercially available and used endoscope control handle and having angulation knobs and levers;

FIG. 3 is an isometric view of the newly disclosed endoscope control handle with oversized angulation knobs/levers;

FIG. 8 is an isometric view of the top of yet another embodiment of the enlarged angulation knob;

FIG. 9 is an isometric view of the bottom of yet another embodiment of the enlarged angulation knob;

FIG. 10 is an isometric view of the top of yet another embodiment of the enlarged angulation knob;

FIG. 11 is an isometric view of the bottom of yet another embodiment of the enlarged angulation knob;

FIG. 12 is a perspective view of the disclosed endoscope handle;

FIG. 13 is a side view of the disclosed endoscope handle;

FIG. 14 is a partial sectional view of the endoscope handle;

FIG. 15 is an isometric view of an alternative embodiment;

FIG. 20 is a side view of yet another embodiment showing a hand operating the endoscope handle;

FIG. 21 is a side view of a small diameter embodiment of the endoscope handle of FIG. 20;

FIG. 22 is a side view of a medium diameter embodiment of the endoscope handle of FIG. 20;

FIG. 23 is a side view of a large diameter embodiment of the endoscope handle of FIG. 20;

FIG. 24 is a side view of the small diameter embodiment of FIG. 21;

FIG. 25 is a side view of the medium diameter embodiment of FIG. 22;

FIG. 26 is a side view of the large diameter embodiment of FIG. 23, wherein the dotted lines show the diameter of the embodiments of FIGS. 21-23;

FIG. 27 is a top view of a small diameter different embodiment;

FIG. 28 is a top view of a medium diameter different embodiment;

FIG. 29 is a top view of a large diameter different embodiment, where the dotted lines show the diameter of the embodiments of FIGS. 27-29;

FIG. 30 is an isometric top view of the FIGS. 27-29 embodiments;

FIG. 31 is an isometric bottom view of the FIGS. 27-29 embodiments showing yet another attachment design;

FIG. 32 is a side view of an endoscope handle using an arcuate top design;

FIG. 33 is a side view of an endoscope handle using a flat top design;

FIG. 43 is a side view of the disclosed endoscopic handle having a palm support strap wrapped around the handle with a palm support bulge and finger gripping surface;

FIG. 44 is a side view of the palm support strap of FIG. 43 showing the elastic palm support bulge being flexed;

FIG. 45 is a plan view of the palm support strap itself;

Figure 4:
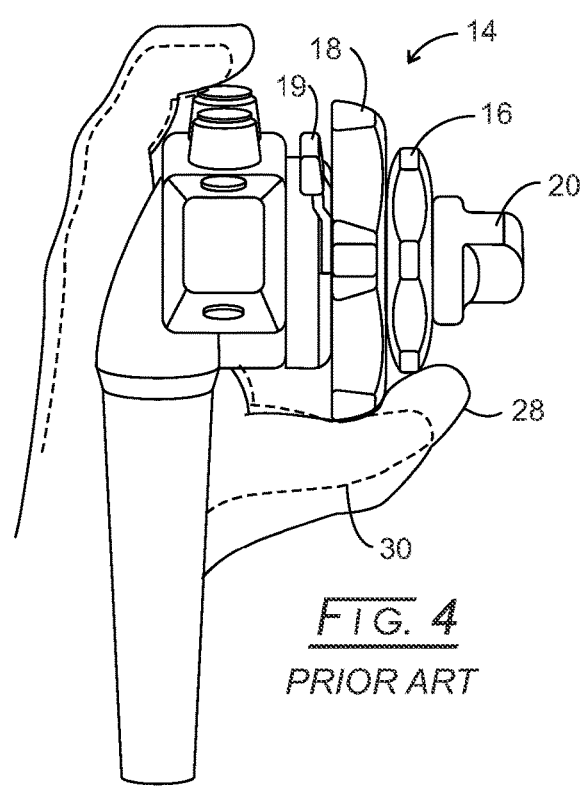
FIG. 4 is an elevation view of the prior art endoscope handle of FIG. 2.

The drawings will be described in greater detail below.

DETAILED DESCRIPTION OF THE INVENTION

Here, we propose a set of accessory devices to directly address these current shortfalls in the design of flexible endoscopes used in practice today and in proposed ergonomic solutions. These accessory devices do not alter the function of the flexible endoscope itself; rather, they augment the performance of flexible endoscopes to perform more safely (to the endoscopist) and efficiently by offering a comprehensive and customizable ergonomic system whose individual components are designed to work together to accommodate the natural variability in human hands, fingers, and anatomy. The comprehensive endoscopic ergonomic system is comprised of two components that are designed to work in tandem, as is disclosed below.

Accessory Devices for the Endoscope Control Wheels

FIG. 1 illustrates a physician, 10, using a conventional endoscope with 2 channels to view, for example, ulcers in a patient, 12, who is lying on his side. Importantly, physician 10 needs to use both hands for the procedure. Physician 10 uses his/her right hand to insert the endoscope channels into patient 12 through the mouth and into the stomach. Control of the angulation of each cardinal axis is controlled by the left hand of physician 10. Of course, the hands may be reversed as shown in FIG. 1. Nevertheless, if the hands of physician 10 are too small to reach both angulation knobs, the physician would need to use his/her right hand to permit control of the angulation knobs; thus, preventing physician 10 to continue inserting the endoscope into patient 12 with the right hand. Clearly, there is a need for angulation knobs easily reachable even by a physician with smaller hands.

FIG. 2 shows a conventional endoscope control handle, 14. Knobs, 16 and 18, are used to control, respectively, left/right movement and up/down movement of the endoscope ends in a patient. A lock knob, 20, retains angulation knob 16, while a tab, 19, retains angulation knob 18 in their respective positions on control handle 14. A specimen access, 22, is provided.

In FIG. 3, a new control handle, 24, is shown having a larger diameter angulation knob, 26, that fits over angulation knob 16. Its larger diameter, at least as large in diameter as control knob 18, permits physicians with small hands to be able to readily reach both angulation knobs.

Figure 5:
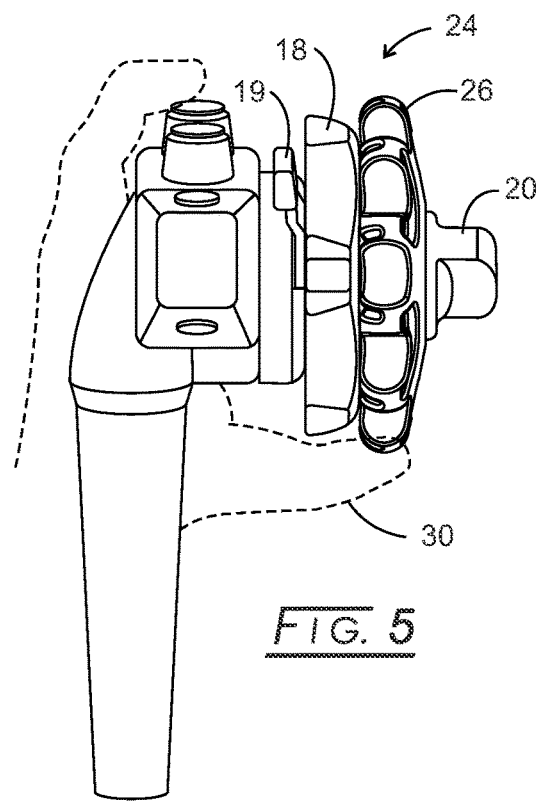
FIG. 5 is an elevation view of the new endoscope control handle of FIG. 3.

The problem to be solved of the angulation knobs of endoscopes can be more readily appreciated by comparing the prior art version in FIG. 4 with the new version in FIG. 5. Initially, a larger physician's hand, 28, is seen easily accessing smaller top angulation knob 16. However, a small physician's hand, 30 (dotted lines), can be seen unable to reach top angulation knob 16. In FIG. 5, oversized angulation knob 26 that fits over smaller top angulation knob 16 has a larger diameter to permit smaller hand 30 (dotted line) to easily reach and rotate both angulation knobs.

Figure 6:
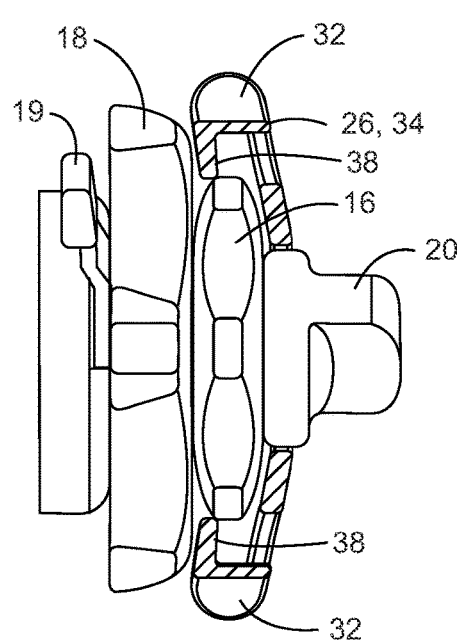
FIG. 6 is a partial sectional view of the new endoscope control handle of FIG. 3.
Figure 7:
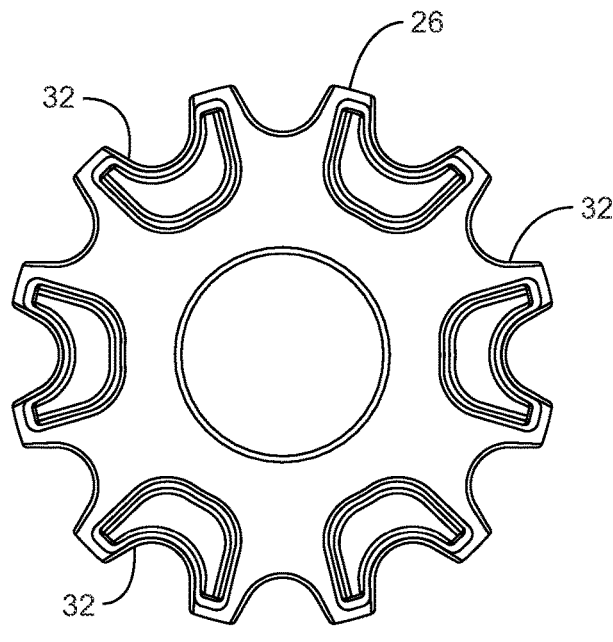
FIG. 7 is a top view of one embodiment of the enlarged angulation knob.

As more clearly seen in FIGS. 6 and 7, there are detents 32, labeled for ease in understanding around the periphery of control knob 26 to enable the user to rotate knob 26 precisely and easily.

Two different embodiments of angulation knob 26 are illustrated in FIGS. 8 and 9, and in FIGS. 10 and 11. Referring initially to the FIGS. 8 and 9 embodiment of an oversize angulation knob, 34, is seen to have a series of downwardly projecting tabs, 36 being labeled for understanding. Cover knob 34 is shown having 6 such tabs that align with detents in knob 16 to create a positive lock for rotation. There are also tabs, 38 that extend inwardly that flex to ensure that cover knob 34 will snap over angulation knob 16 (FIG. 6). Openings, 35 on the top outer surface of knob 34 enable the tabs 38 to flex.

An alternative embodiment of a cover knob, 40, is shown in FIGS. 10 and 11. In this embodiment the downwardly projecting tabs 42 being labeled for understanding. These tabs 42 also project downwardly from an inner surface, 46, of cover knob 40. Cover knob 34 is shown having 6 such tabs that alien with detents in knob 16 to create a positive lock for rotation. An opening 44 in the bottom of knob 40 fits over knob 16 but does not have the ability to readily flex, but still provide the ability of cover knob 40 to snap into position over top angulation knob 16 so that rotating cover knob 40 results in a simultaneous and identical rotation of top angulation knob 16. Its larger diameter, however, makes cover knob 40 easier to reach by physicians with smaller hands.

Referring now to FIGS. 12-14, a top cover angulation knob, 48, fits over top angulation knob 16 and a bottom angulation knob, 52 fits over bottom angulation knob 18. The diameter of knob 48 is at least as large as the diameter of bottom angulation knob 52, permits the small hand 30 reach both control knobs readily. Again, as illustrated in FIG. 14, top cover knob 48 is seen fitted over smaller top angulation knob 16. Its larger diameter compared to lower angulation knob 52 also is readily appreciated.

Figure 16:
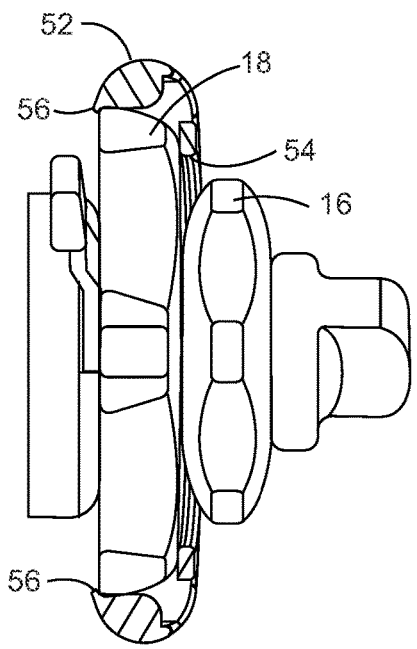
FIG. 16 is a partial sectional view of the alternative embodiment of FIG. 15.
Figure 17:
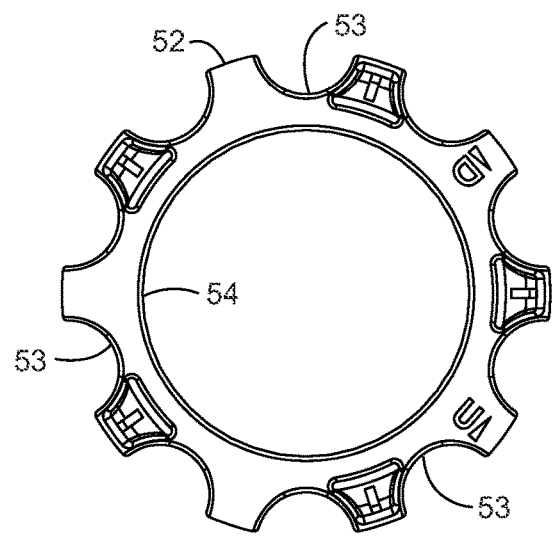
FIG. 17 is a top view of a further embodiment.
Figure 18:
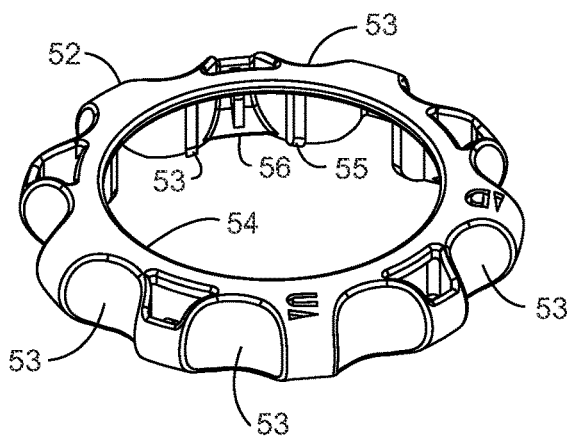
FIG. 18 is an isometric view of the further embodiment of FIG. 16.
Figure 19:
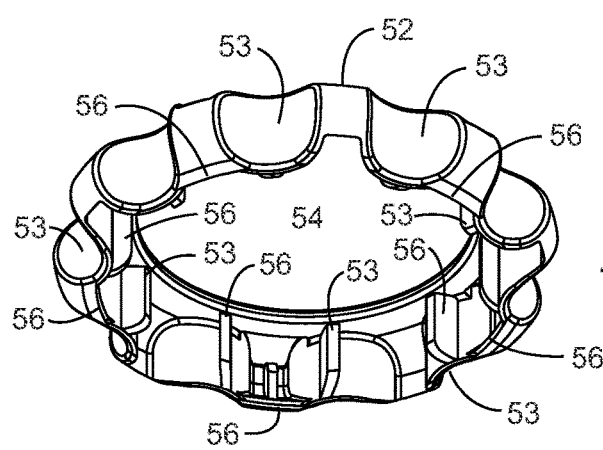
FIG. 19 is an isometric view looking at the bottom of the further embodiment.

A control handle, 50, is seen in FIGS. 15 and 16 and illustrates the fitment of the bottom cover knob, 52, and knob 52 is also illustrated in FIGS. 17-19. Cover control knob 52 has a series of outer diameter detents 53 for the physician's fingers. A series of inwardly projecting tabs (tabs 53 and 55 only labeled) can be seen for aligning cover control knob 52 over bottom angulation knob 18. Control knob 52 has a large opening 54 in its top to clear knob 16. Tabs 56 snap over knob 18 securing knob 52 to knob 18.

FIGS. 20-26 illustrate yet a further series of top cover embodiments. In particular, top cover knobs, 58A, 58B, and 58C, are identical in design and construction. The difference is the diameter of each top cover knob. Top cover knob 58A is relatively small is size; top cover knob 58C is relatively large is diameter; and top cover knob 58B has a diameter therebetween.

Top cover knobs, 60A, 60B, and 60C, are illustrated in FIGS. 27-31. Initially, it will be observed that top cover knob 60A is relatively small in size and, thus, is labelled "S". Top cover knob 60C is relatively larger in size and, thus, is labelled "Lg" for large. Top cover knob 60B is medium in size compared to top cover knobs 60A and 60C, and, thus, is labeled with "M" for being medium in size.

The design and construction of any top cover knob 60 is seen in FIGS. 30 and 31 to have downwardly projecting tabs 62 and inwardly projecting knobs 64 similarly to those taps 36 and 38 shown in FIGS. 8 and 9. The series of 6 tabs 64 snap over top angulation knob 16 and hold it in place.

A top cover knob, 66, in FIG. 32 has a convex shape top surface; while a top cover knob, 68, in FIG. 33 has a relatively flat top surface. Again, the manufacturer has great flexibility in design and construction of the disclosed top cover knobs.

The accessory device may be designed with a honeycomb structure to minimize weight and maximize structural integrity and aesthetics. In addition, this honeycomb structure results in tactile and ergonomic advantages that are designed specifically to work with soft device accessories for the endoscope control handle (below) to provide a completely customizable ergonomic solution. The dimensions of the control wheel accessories are calibrated precisely to allow clearance for each control wheel accessory to work with each other and to allow application and function of soft device accessories for the endoscope control handle to work.
Soft Accessory Devices for the Endoscope Control Handle Improved ergonomics in endoscopy are achieved by keeping the hand as close to a neutral anatomic position as possible and through support of the hand while grasping the endoscope handle. A soft goods-based solution can attach to the control handle and allow the endoscopist's hand to rest in a more neutral position while performing endoscopy, such as is illustrated in FIGS. 34-49. In addition, a soft goods-based solution can support the hand while grasping the endoscope (see FIGS. 34-39).

These ergonomic goals are accomplished through multiple solutions that fill the space between the palm of the left hand and the control handle itself and support the hand and fingers in natural positions (see FIGS. 34-49). Much of what is successful from an ergonomic perspective will be determined by personal preference. As such, multiple solutions are needed to accommodate an endoscopist's preference. In addition, a soft goods solution (as opposed to a solution with a hard component) minimizes damage to the endoscope and provides maximal conformability to the endoscopists hand. In addition, a soft goods design results in tactile and ergonomic advantages that are designed specifically to work with the control wheel accessories to provide a completely customizable ergonomic solution.

The two components of this comprehensive ergonomic endoscopic solution, the control wheel accessory devices and the control handle accessory devices, are designed to work in concert with each other to deliver the best ergonomic solution considering multiple configurations for different control wheel accessory placement and sizes and different soft goods solutions (representative combined solution shown in FIGS. 34-49). Only a comprehensive solution whereby the components are designed to function together as a whole can improve ergonomics to the fullest. These components can be individualized by selecting different sizes and configurations that each endoscopist can select for best performance.

In summary, the accessory devices described provide a comprehensive ergonomic endoscopic solution augmenting the function of current endoscopes. This is done by directly addressing the shortcomings of the 'one size fits all' design approach used in endoscope manufacture, which fail to account for the natural variability in human hand and/or finger sizes. The comprehensive ergonomic endoscope solution described can augment the performance of multiple different endoscopes with different purposes (i.e., gastroscopes, colonoscopes, duodenoscopes, echoendoscopes, etc.). These accessory devices will help address potential endoscopist injuries and ergonomic efficiencies by offering an array of effective natural sizes for accessorized endoscope control wheels and control handle.

Figure 35:
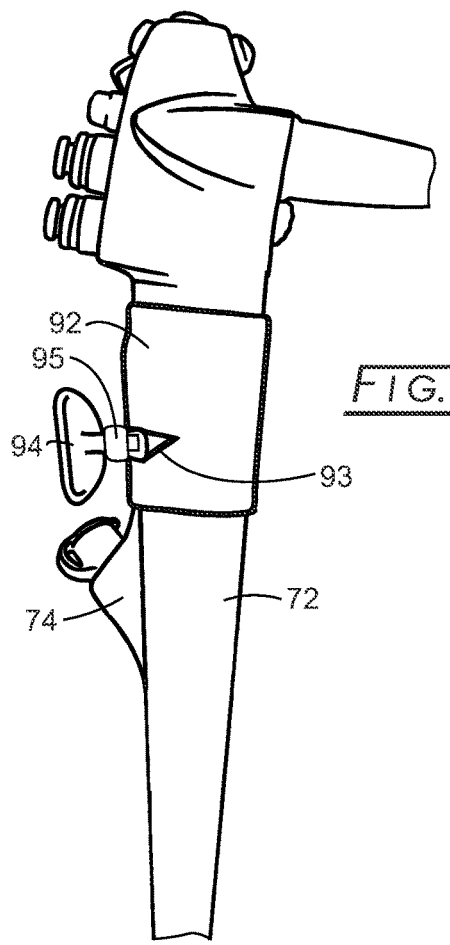
FIG. 35 is a side view of the endoscope handle shown in FIG. 34.
Figure 36:
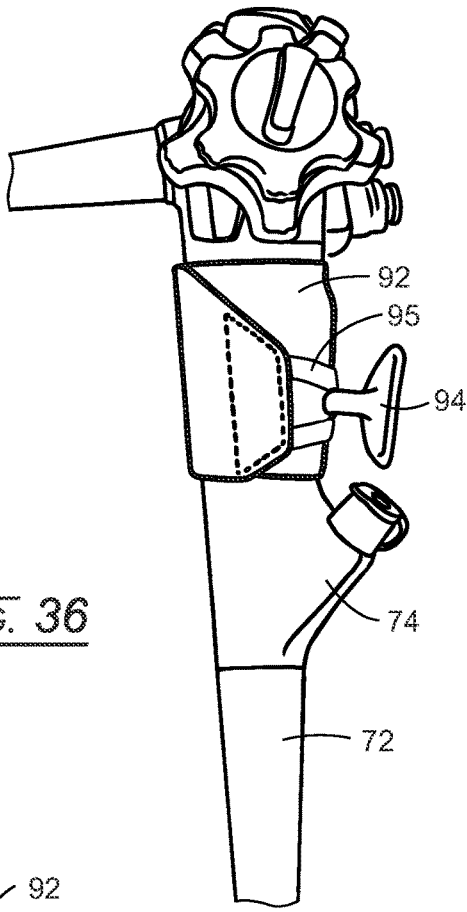
FIG. 36 side view of the opposite side of the endoscope handle shown in FIG. 35.

Referring now to FIGS. 34-49, a hand, 70, is seen grasping a handle, 72, of an endoscope having a specimen port, 74, and conventional angulation knobs, 76 and 78 (see also FIG. 36). These items will not be repeated for each of the drawings. In each embodiment illustrated, a different soft goods attachment that fills the space between the palm of the left hand and the control handle itself and support the hand and fingers in natural positions. A mirror image of the configurations in the drawings would be applicable for a handle grasped by the right hand.

Figure 34:
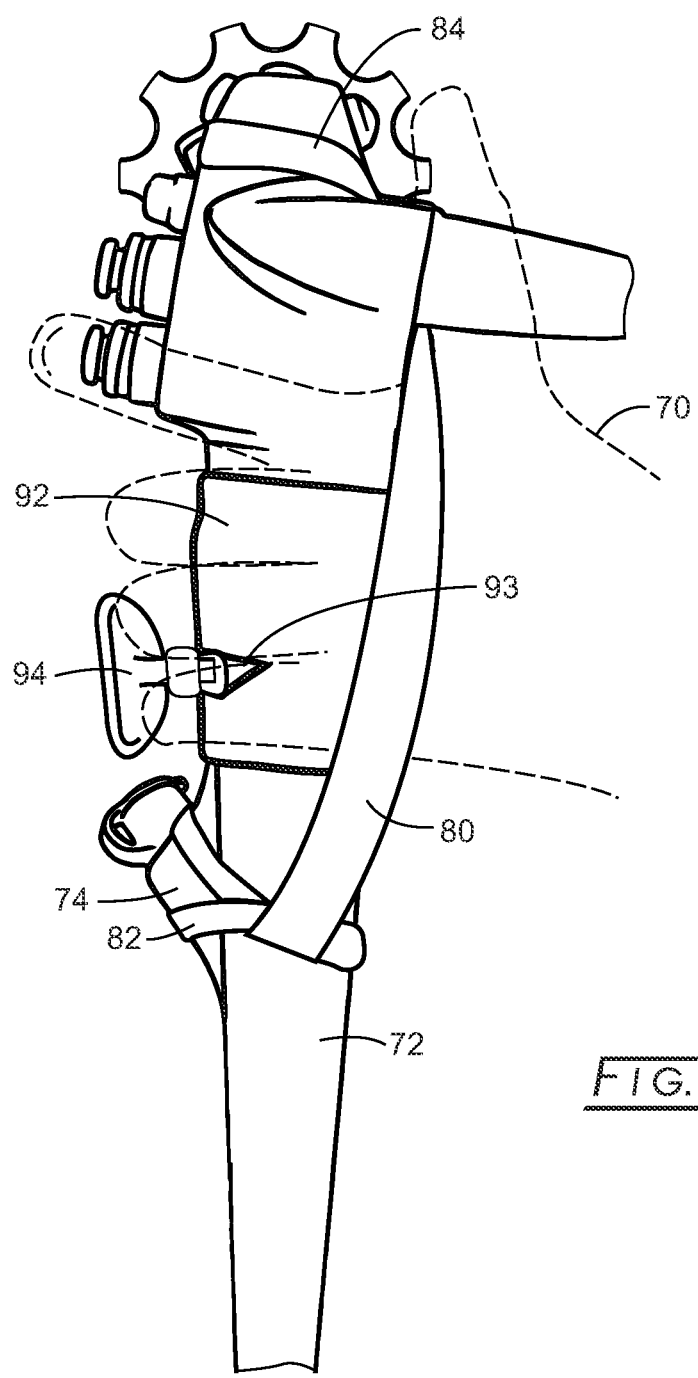
FIG. 34 is a side view of a physician's hand holding an embodiment of the disclosed endoscope handle having a wrap-around elastic member for cushioning and locating the hand on the handle.

In FIG. 34, an elastic strap, 80, wraps around handle 72 with a lower loop, 82, wrapping around specimen port 74 and an upper loop, 84, wrapping around handle 72 just below angulation knobs 76 and 78 (again, see also FIG. 36). Elastic strap 80 desirably is made from a foamed elastomer for cushioning of hand 70 (shown in phantom) and its fingers.

Referring now to both FIGS. 34-36, a wrap-around elastic band, 92, wraps around the central portion of handle 72 cushioning the palm of hand 70. Additionally, a slit, 93, in band 92 permits rigid finger leverage adapter, 94, to fit therethrough with the tightness of elastic band 92 hold rigid finger leverage adapter 94 securely in place. This embodiment provides superior neutral hand positioning, hand cushioning, and customized angulation knobs to the user. As seen in FIG. 36, elastic strap 80 has a loop array at one of its ends and a hook array at its other end for its attachment to handle 72. Such hook and loop attachment combination is illustrated by a VELCRO® strap.

Figure 37:
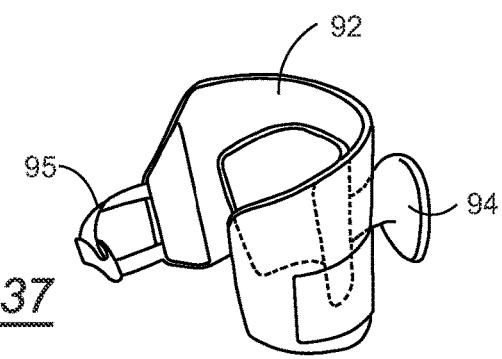
FIG. 37 is an isometric view of the wrap-around elastic member shown in FIG. 34.
Figure 38:
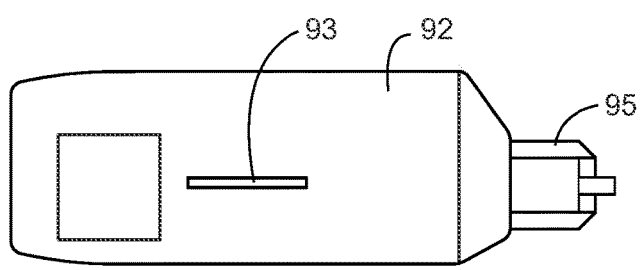
FIG. 38 is a side view of the elastic member shown in FIG. 37.

FIGS. 37 and 38 is an isometric view of elastic strap 92 and rigid finger leverage adapter 94. To aid in undoing a secured hook and loop closure assembly, elastic strap 80 and has a pull tab, 95, extending from either the hook or the loop closure end of elastic strap 92 since such closure structures can be difficult to undo.

Figure 39:
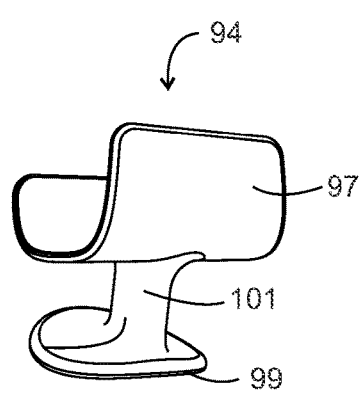
FIG. 39 is an isometric view of a rigid finger leverage adapter for use in conjunction with the elastic member of FIG. 37.

In FIG. 39 shows rigid finger leverage adapter 94 in isometric view. Adapter 94 has an upper saddle-shaped finger rest, 97, a base, 99, and a neck, 101. Neck 101 fits through slit 93. Base 99 is held secure by elastic strap 92.

Figure 40:
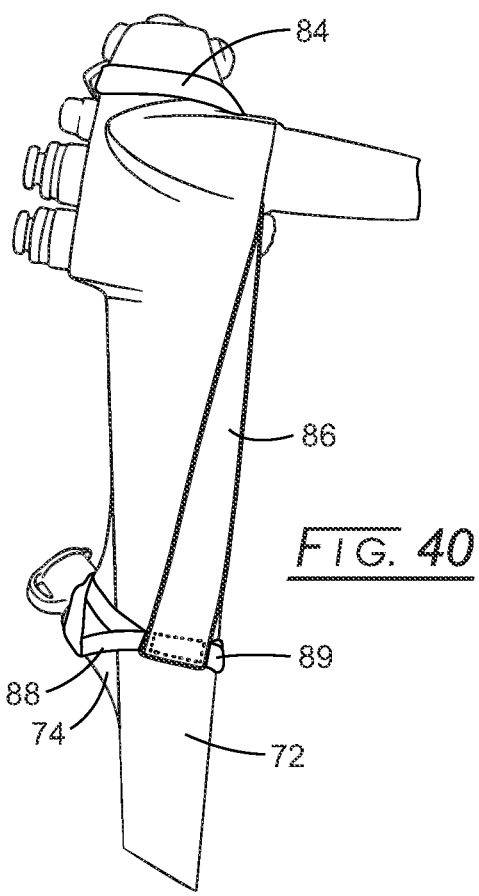
FIG. 40 is a side view of the disclosed endoscopic handle fitted with an elastic hand strap for wrapping around the physician's hand grasping such handle.
Figure 41:
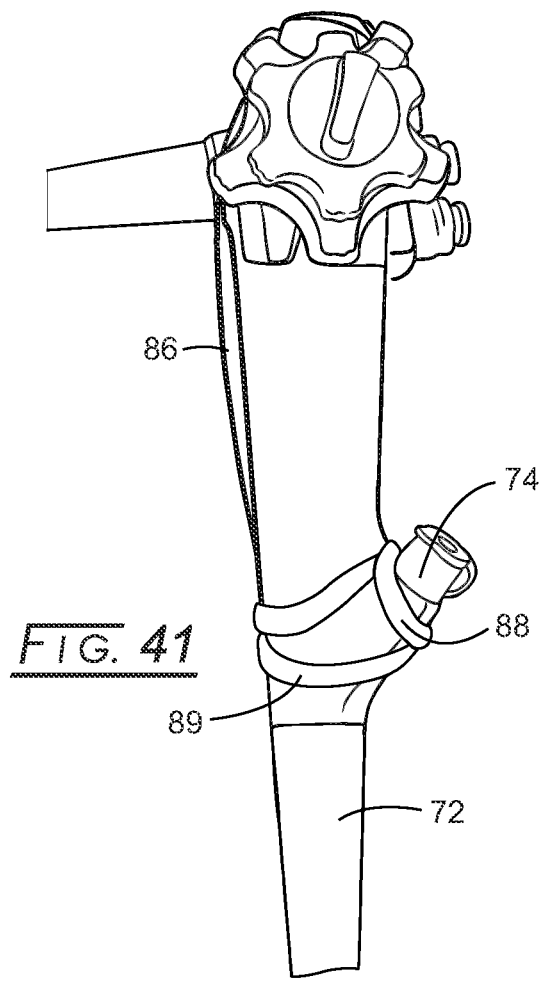
FIG. 41 is a front view of endoscopic handle and hand elastic strap shown in FIG. 40.
Figure 42:
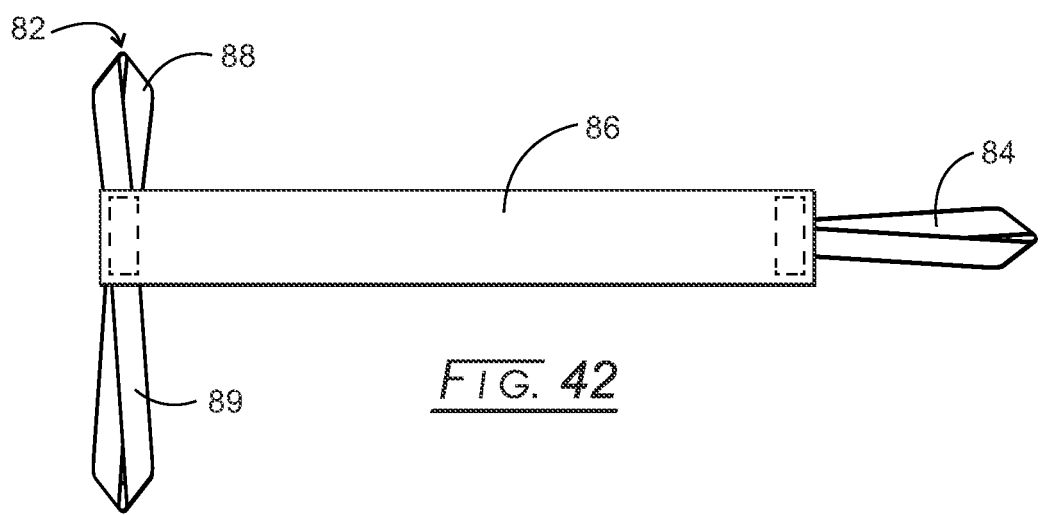
FIG. 42 is a plan view of the elastic hand strap of FIGS. 40 and 41.
Figure 46:
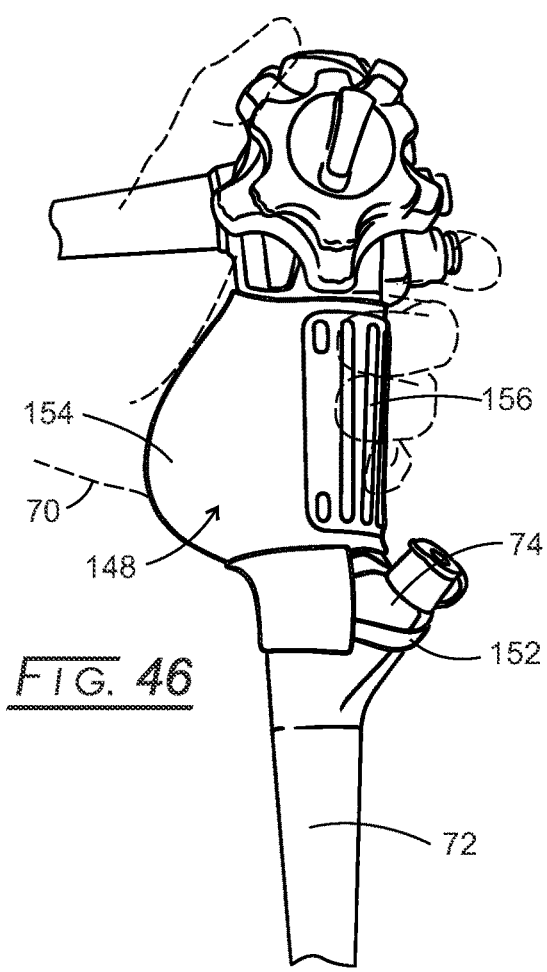
FIG. 46 is an alternative palm support strap wrapping around the endoscopic handle with a physician's hand grasping the handle.
Figure 47:
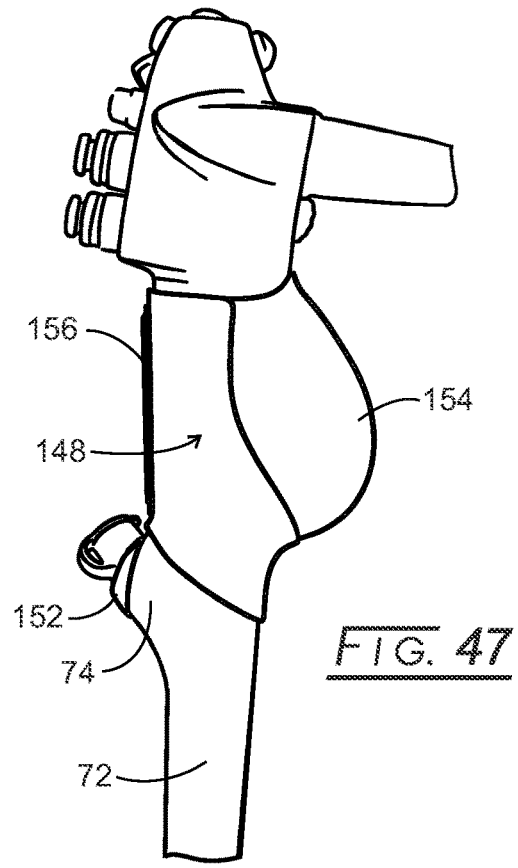
FIG. 47 is a side view of the other side of the endoscopic handle and alternative palm support strap without the physician's hand.
Figure 48:
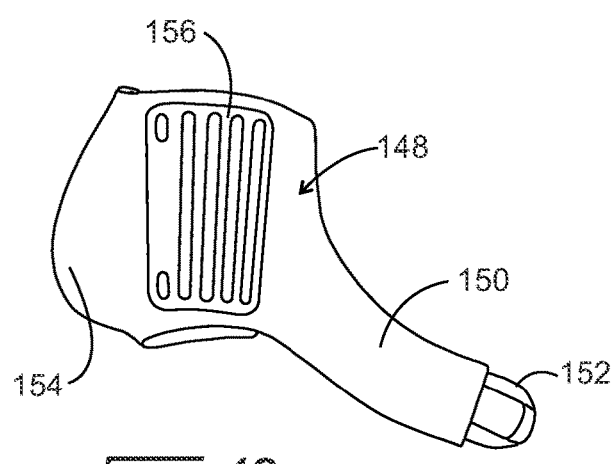
FIG. 48 is a side view of the alternative palm support strap of FIG. 46.
Figure 49:
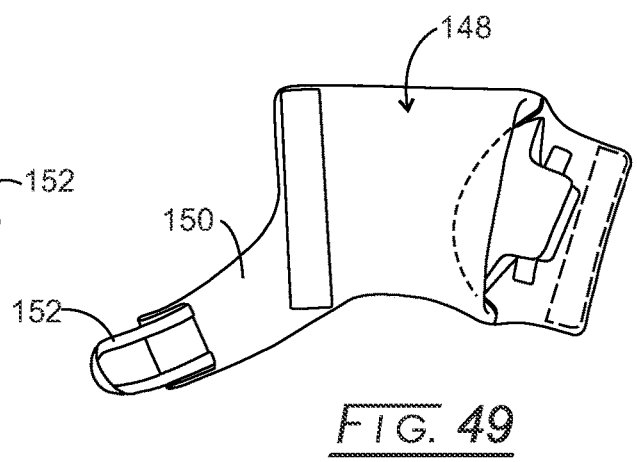
FIG. 49 is a side view of the opposite side of the view of the alternative palm support strap shown in FIG. 48.

Referring to FIGS. 40-42, an alternative elastic strap hand retention assembly is illustrated. In particular, elastic strap, 86, is designed to surmount the hand of the physician so that handle 72 will not drop should the physician let loose of the grip on handle 72. Elastic strap 86 is secured about the top end of handle 72 by a loop, 90, and at the lower end of handle 72 by a pair of loops, 88 and 89, that fit around specimen port 74.

Referring now to FIGS. 43-45, a hand cushioning strap, 136, fits about handle 72 below the angulation knobs and port 74. Strap 136 has a pair of ribbed patches, 138 and 140, that aid in keeping hand 70 from slipping when holding handle 72. Additionally, strap 136 has a palm pad, 142, to provide hand 70 with cushioning and hold hand 70 in a more neutral position to help prevent hand fatigue.

Referring now to FIGS. 46-49, an alternative cushioning elastic strap, 148, that carries a lower strap assembly, 150, extending from the main body of strap 148 and terminating with a loop, 152, that fits around specimen port 74. A palm pad, 154, protrudes outwardly from the main body of strap 148 for comforting hand 70 and helping prevent hand fatigue. A ribbed patch, 156, aids in preventing hand 70 from slipping during use of handle 70. A similar ribbed patch may be provided opposite ribbed patch 156. Elastic strap 148 is closed around handle 70 using hook and loop ends or any other close assemblies as is necessary, desirable, or convenient.

It will be readily apparent that any of the attachments of FIGS. 34-49 can be combined with any of the novel angulation knob covers to provide superior neutral hand positioning, hand cushioning, and customized angulation knobs to the user.

While the apparatus, system, and method have been described with reference to various embodiments, those skilled in the art will understand that various changes may be made and equivalents may be substituted for elements thereof without departing from the scope and essence of the disclosure. In addition, many modifications may be made to adapt a particular situation or material in accordance with the teachings of the disclosure without departing from the essential scope thereof. Therefore, it is intended that the disclosure not be limited to the particular embodiments disclosed, but that the disclosure will include all embodiments falling within the scope of the appended claims. In this application all units are in the metric system and all amounts and percentages are by weight, unless otherwise expressly indicated. Also, all citations referred herein are expressly incorporated herein by reference.

REFERENCES

ADDIN ZOTERO_BIBL {"uncited":[ ],"omitted":[ ],"custom":[ ]} CSL_BIBLIOGRAPHY 1. Gastrointestinal Endoscopic Devices Market Analysis, Size, Trends-|Global|2019-2025|MedSuite. *iData Research* https://idataresearch.com/product/gastrointestinal-endoscopic-devices-market/.
2. Berguer, R. & Hreljac, A. The relationship between hand size and difficulty using surgical instruments: a survey of 726 laparoscopic surgeons. *Surg. Endosc.* 18, 508-512 (2004).
3. Ratuapli, S. et al. Kinematic analysis of wrist motion during simulated colonoscopy in first-year gastroenterology fellows. *Endosc. Int. Open* 03, E621-E626 (2015).
4. Siau, K. & Anderson, J. T. Ergonomics in endoscopy: Should the endoscopist be considered and trained like an athlete? *Endosc. Int. Open* 07, E813-E815 (2019).
5. Austin, K. et al. Musculoskeletal Injuries Are Commonly Reported Among Gastroenterology Trainees: Results of a National Survey. *Dig. Dis. Sci.* 64, 1439-1447 (2019).
6. Shergill, A. K., McQuaid, K. R. & Rempel, D. Ergonomics and GI endoscopy. *Gastrointest. Endosc.* 70, 145-153 (2009).
7. Cappell, M. S. & Co, M. Endoscopes for endoscopists with small hands: a call to meet an unmet demand. *Gastrointest. Endosc.* 78, 670-672 (2013).
8. Shergill, A. K. & McQuaid, K. R. Ergonomic endoscopy: An oxymoron or realistic goal? *Gastrointest. Endosc.* 90, 966-970 (2019).

The invention claimed is:

1. A device for improving ergonomics of an endoscopic control handle, the device comprising:
   a first strap having an inner surface and an outer surface, wherein the first strap forms an upper loop that is directly couplable to a top end of the endoscopic control handle, wherein the upper loop is freely rotatable about a portion of the endoscopic control handle;
   a lower loop extending from the first strap, the lower loop configured to wrap around and connect to a lower end of the endoscopic control handle adjacent to a specimen port;
   a wrap-around elastic band configured to wrap around a central portion of the endoscopic control handle to cushion a palm of a hand; and
   a finger leverage adapter having a base, a neck, and a finger rest, wherein the wrap-around elastic band further comprises a slit such that the finger rest and the neck of the finger leverage adapter fits through the slit when the finger leverage adapter is installed underneath the wrap-around elastic band,
   wherein the inner surface of the first strap and the endoscopic control handle together define a hand space configured to accept a user's hand such that a dorsal side of the hand abuts the inner surface of the first strap and a palm side of the hand abuts the endoscopic control handle, and
   wherein the device is dimensioned such that the user's hand is secured within the hand space in a neutral position and the user's thumb is not covered by the first strap such that the user's thumb can freely move to operate the endoscopic control handle.

2. The device of claim 1, wherein the lower loop extends substantially perpendicular from the first strap.

3. The device of claim 1, wherein the lower loop comprises a loop configured to wrap around the specimen port of the endoscopic control handle.

4. The device of claim 1, wherein at least one of the first strap and the lower loop comprises a hook-and-loop closure.

5. The device of claim 1, further comprising a palm pad protruding outwardly from the wrap-around elastic band into the hand space, the palm pad being shaped to fill the hand space between a user's palm and the endoscopic control handle.

6. The device of claim 1, wherein the palm pad further comprises a ribbed patch configured to prevent slipping of the user's hand.

7. A system comprising:
   a knob cover configured to fit over a top angulation knob of an endoscopic control handle, the knob cover comprising:

a top surface defining a central opening centered about a central axis;
an inner surface opposite of the top surface;
a plurality of downwardly projecting tabs projecting from the inner surface;
a plurality of detents arranged around a periphery of the knob cover; and
a plurality of tabs extending inwardly from the periphery towards the central axis, the plurality of tabs extending inwardly comprising a free end engageable with the top angulation knob,
wherein a primary diameter about the periphery of the knob cover is larger than a first diameter of the top angulation knob; and
a device for improving ergonomics of the endoscopic control handle, the device comprising:
a first strap having an inner surface and an outer surface, wherein the first strap forms an upper loop that is directly couplable to a top end of the endoscopic control handle, wherein the upper loop is freely rotatable about a portion of the endoscopic control handle;
a lower loop extending from the first strap, the lower loop configured to wrap around and connect to connect to a lower end of the endoscopic control handle adjacent to a specimen port;
a wrap-around elastic band configured to wrap around a central portion of the endoscopic control handle to cushion a palm of a hand; and
a finger leverage adapter having a base, a neck, and a finger rest, wherein the wrap-around elastic band further comprises a slit such that the finger rest and the neck of the finger leverage adapter fits through the slit when the finger leverage adapter is installed underneath the wrap-around elastic band,
wherein the inner surface of the first strap and the endoscopic control handle together define a hand space configured to accept a user's hand such that a dorsal side of the hand abuts the inner surface of the first strap and a palm side of the hand abuts the endoscopic control handle,
wherein the device is dimensioned such that the user's hand is secured within the hand space in a neutral position and the user's thumb is not covered by the first strap such that the user's thumb can freely move to operate the endoscopic control handle, and
wherein the knob cover and the device for improving ergonomics of the endoscopic control handle are configured to work in tandem to provide an ergonomic grip and hand position to a user of the endoscopic control handle.

8. The system of claim 7, wherein the device is configured to place a user's thumb adjacent to the knob cover in the neutral position.

9. A device for improving ergonomics of an endoscopic control handle, the device comprising:
a first strap having an inner surface and an outer surface, wherein the first strap is couplable to a top end of the endoscopic control handle;
a lower loop extending from the first strap, the lower loop configured to connect to a lower end of the endoscopic control handle adjacent to a specimen port;
a wrap-around elastic band configured to wrap around a central portion of the endoscopic control handle to cushioning a palm of a hand; and
a finger leverage adapter having a base, a neck, and a finger rest, wherein the wrap-around elastic band further comprises a slit such that the finger rest and the neck of the finger leverage adapter fits through the slit when the finger leverage adapter is installed underneath the wrap-around elastic band,
wherein the inner surface of the first strap and the endoscopic control handle together define a hand space configured to accept a user's hand such that a dorsal side of the hand abuts the inner surface of the first strap and a palm side of the hand abuts the endoscopic control handle, and
wherein the device is dimensioned such that the user's hand is secured within the hand space in a neutral position.

* * * * *

UNITED STATES PATENT AND TRADEMARK OFFICE
CERTIFICATE OF CORRECTION

| | | |
|---|---|---|
| PATENT NO. | : 12,349,862 B2 | Page 1 of 1 |
| APPLICATION NO. | : 17/597783 | |
| DATED | : July 8, 2025 | |
| INVENTOR(S) | : Benjamin K. Poulose | |

It is certified that error appears in the above-identified patent and that said Letters Patent is hereby corrected as shown below:

On the Title Page

Page 2, Column 2, Line 17 of item [56], Other Publications, delete "Gastrointest," and insert -- Gastrointest. --

In the Claims

In Column 10, Line 61 Claim 6, delete "claim 1," and insert -- claim 5, --

Signed and Sealed this
Fourth Day of November, 2025

John A. Squires
*Director of the United States Patent and Trademark Office*